United States Patent [19]

Roberts et al.

[11] Patent Number: 4,728,608

[45] Date of Patent: Mar. 1, 1988

[54] BACTERIAL SCREENING SYSTEM WITH ENHANCED SHELF LIFE

[75] Inventors: John W. Roberts, Milford; Karen E. DeBell, Easton, both of Mass.

[73] Assignee: Cambridge BioScience Corporation, Worcester, Mass.

[21] Appl. No.: 720,757

[22] Filed: Apr. 8, 1985

[51] Int. Cl.[4] .......................... C12Q 1/04; C12Q 1/32
[52] U.S. Cl. ........................................ 435/34; 435/26; 435/810
[58] Field of Search .................. 435/34, 810, 26, 183, 435/36, 37, 38, 25, 27, 28

[56] References Cited

U.S. PATENT DOCUMENTS

| | | | |
|---|---|---|---|
| 3,326,777 | 7/1967 | Babson | 435/26 |
| 3,732,147 | 5/1973 | Fosker et al. | 435/26 |
| 4,026,767 | 5/1977 | Shih et al. | 435/26 |
| 4,120,755 | 10/1978 | Pierre et al. | 435/26 |
| 4,129,483 | 12/1978 | Bochner | 435/34 |
| 4,556,634 | 12/1985 | Misaki et al. | 435/26 |

*Primary Examiner*—Sidney Marantz
*Assistant Examiner*—William J. Herald
*Attorney, Agent, or Firm*—Bromberg, Sunstein & Casselman

[57] ABSTRACT

A tetrazolium-based system for testing for the presence of organisms or cells in a specimen includes in one embodiment a mixture of a substrate and an indicator system, wherein the overall system is buffered to a pH above 8.0, and in a preferred embodiment at about a pH of 9.0 when mixed. The substrate solution and indicator solution are not mixed until shortly before use. The indicator solution is buffered at a pH of approximately 3.3, thereby enhancing the shelf life. The substrate may consist of glucose with at least one amino acid in a buffered solution formulated such that, by mixing equal parts with the indicator solution, a pH above 8, preferably 9.0 results.

3 Claims, No Drawings

BACTERIAL SCREENING SYSTEM WITH ENHANCED SHELF LIFE

DESCRIPTION

1. Technical Field

The present invention relates to assays for the presence of organisms, particularly bacteria, in specimens taken from sources such as biological fluids, water, and food.

2. Background Art

It is known in the art to use a tetrazolium salt as a component in a system for identifying the presence of bacteria in fluid specimens. Such a system is based upon the reduction/oxidation reactions which occur as bacteria ferment and perform oxidative phosphorylation of high energy nutrients (i.e., carbohydrates) and linking them to indicators which develop color upon reduction or oxidation:

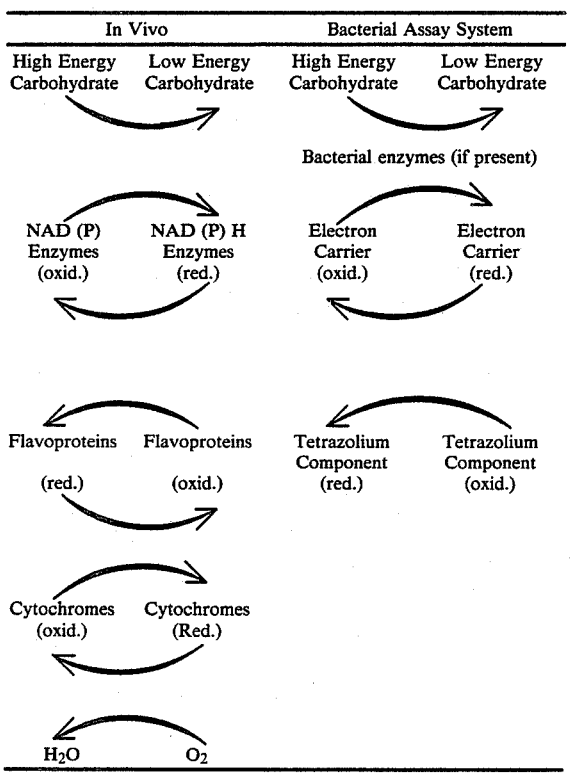

When a tetrazolium compound is reduced, a highly insoluble intensely colored formazan is formed, permitting the presence of bacteria to be identified on direct visual inspection after an incubation period.

The in vivo purpose of the cascade-like breakdown of high energy components is to trap the energy stored therein as ATP. Each transfer component has a progressively higher reduction/oxidation potential than the components preceding it in the cascade. In tetrazolium-based assays, the NAD (P) dehydrogenases generally reduced tetrazolium dyes poorly when directly coupled, but when intermediate electron carriers are used, the reduction of the tetrazolium dye to the colored formazan occurs more rapidly.

It is also known to use, for the substrate for bacterial growth, Schaedler broth (Difco) which is a solution of tryptic soy broth, proteose peptone no. 3, yeast extract, dextrose, tris(hydroxy-methyl)amino methane, L-cystine, and hemin; the solution has a physiologically typical pH in the range of 7.0–7.5.

Prior art tetrazolium-based bacterial assays have typically been plagued by a number of disadvantages, making such assays difficult to employ in individually packaged disposable test kits for mass distribution. First, the shelf-life of tetrazolium solutions is generally short—less than six months even under refrigeration. Second, the sensitivity of such assays of urine specimens is typically not better than about $10^6$ colony forming units (CFU)/ml., which is not sufficiently high sensitivity for many clinical purposes. Third, such assays may also produce non-specific background color development, which can interfere with ready, direct visual observation of the colored formazan.

DISCLOSURE OF INVENTION

The present invention provides a tetrazolium-based system, overcoming disadvantages in prior art systems, for testing for the presence of organisms in a specimen, wherein the overall system, including a mixture of a substrate and an indicator system, is buffered to a pH above approximately 8.0. In a preferred embodiment of the invention, the test system is buffered to a pH of approximately 9.0 and until use is stored as a separate substrate solution, having a high pH and an indicator solution buffered to a pH of approximately 3.3 thereby enhancing the shelf life of the indicator solution. Another embodiment provides a substrate consisting of glucose with at least one amino acid in a buffered solution.

DESCRIPTION OF SPECIFIC EMBODIMENTS

As described in further detail below, a preferred embodiment of the present invention utilizes separate substrate and indicator solutions which are mixed just before use to form the test system. In the examples following, the specimen is typically a 1 ml fluid specimen, such as urine, which is first passed through a course filter to remove large particles that may otherwise interfere with testing, then through a bacterial filter having a porosity sufficient to permit fluid flow, but which traps and concentrates the bacteria. A 1 ml wash solution of saline, phosphate-buffered saline, tris, or other physiologically reasonable buffer is then passed through the same filters. A pH of the wash ranging from 6–9 and molarity ranging from 0.05 to about 0.2 have been found to be uncritical. Quantity of 0.25 to 0.50 ml of the previously mixed test system reagent is then added above the bacterial filter and about 0.1 ml of the test system is passed through the filter, leaving a fluid head above the filter. The bacterial filter with its fluid head is then incubated at 35°–37° C. for periods up to one-half hour. (Temperatures up to 43° C. have produced acceptable results.) The presence of bacteria is determined by direct visual inspection of the surface of the filter, which under such circumstances develops a color ranging from violet to blue-black.

The chemistry described herein is suitable for use in a device, of the type described in co-pending application Ser. No. 709,595, filed Mar. 8, 1985, for an invention of Buck et al., which is hereby incorporated herein by reference. For use in a device of the type therein described, the chambers 16a and 16b of FIGS. 1–3 therein may be used to hold the separate substrate and indicator solutions, which are mixed to form the test system when the device is used.

EXAMPLE 1

A two-part test system that includes (a) an indicator system and (b) a buffered substrate is prepared as follows:

| A. Indicator System | | |
|---|---|---|
| 1. Nitrobluetetrazolium | 23.8 mg | Calbiochem 202945 |
| 2. Phenazine ethosulfate | 9.8 mg | Sigma 13F0041 |
| 3. Deionized water QS to | 70 ml | |
| 4. Dissolve, adjust pH to | 3.3 w/0.1 m HCl | |
| Filter, sterilize and store in the dark at 2-8° C. | | |
| B. Substrate/buffer | | |
| 1. Glucose | 750 mg | Sigma |
| 2. Serine | 150 mg | Sigma |
| 3. Glutamic acid | 255 mg | Sigma |
| 4. Tris base | 1500 mg | Sigma |
| 5. Anhydrous sodium carbonate | 74 mg | Mallinkrodt |
| 6. Deionized water QS | 75 ml | |
| Filter, sterilize, and store at 2-8° C. | | |

Substrate/buffer pH is 8.8 to 9.2 when mixed.

Before use, the test system is prepared by mixing 1 part of the indicator system with 1 part of the substrate/buffer; pH after mixing is between 8.8 and 9.2. The mixture is stored in the dark at 2°-8° C.

Following the procedure set forth above, this test system produced a sensitivity at least as good as $10^5$ colony forming units (CFU) per ml, which corresponds to approximately 95% of urine specimens containing pathogens. This is a preferred embodiment of the invention.

In comparison to a substrate based on Schaedler broth, it was found that the individual presence of any of hemin, yeast, or peptones in the Schaedler formulation at the high pH levels used here caused non-specific background color development. The above buffered substrate (which eliminates all components of the Schaedler formulation determined to be non-essential, and produces a test system with an exceptionally high pH) yielded dramatic improvements over prior art formulations. Increasing the pH of the test system above 9.2 increased sensitivity but also increased spontaneous color development, resulting in a loss of test specificity. The inventors believe that the elevated pH produces improved test results owing to the optimal activity of many bacterial dehydrogenases at these pH levels, even though these levels are in excess of what one might otherwise expect for a physiological system.

EXAMPLE 2

A two-part test system is prepared as in Example 1, but the pH of the indicator system and substrate/buffer are formulated to give the test system a more physiologically typical pH ranging between 7.0 and 7.5. This test system produced a sensitivity of about $10^6$ colony forming units (CFU) per ml.

EXAMPLE 3

A two-part test system is prepared as in Example 1, but the step of adjusting the pH of the indicator system to 3.3 is omitted. The indicator system and the substrate/buffer were each aliquotted into 0.5 ml quantities in separate vials and sealed. Samples were stored at 2°-8° C. (5° C.), 18°-25° C. (20° C.), 35° C., 45° C. Periodically samples were taken by opening and mixture one vial of indicator system and one vial of substrate/buffer. Dilutions (in urine) of a standard bacterial suspension (produced from a stock freezer culture) were used to evaluate potency of the test reagent. A freshly prepared (within 24 hours) reagent was used as a reagent control. A sterile urine was used as a negative bacterial control and historical documentation of the bacterial strain's reactivity coupled with use of fresh reagent served as a positive control. Using the Arrhenius accelerated stability method (a product is generally stable twice as long at 5° C. as it is at 15° C. and four times as long at 5° C. as it is at 25° C., etc.), refrigerated stability was extrapolated. Refrigerated, stability of the test system was found to be less than 6 months, whereas refrigerated stability of the two-part test system prepared in accordance with Example 1 was 2-3 years.

It will be apparent that although Example 1 identifies NBT [2,2',d(p-nitrophenyl)-5,5'diphenyl-3',(3,3'dimethoxy-4,4'diphenylene)ditetrazolium chloride] as the tetrazolium salt and PES as the electron carrier employed, any suitable tetrazolium salt, such as INT [2(p-iodophenyl)3(peranitrophenyl)5phenyl tetrazolium chloride], TNBT [2,2',5,5'tetra-(p-nitrophenyl)-3,3'(dimethoxy-4'diphenylene)di-tetrazolium chloride], or MTT, and any suitable electron carrier, such as PMS (phenazine methosulfate) or meldola blue, may be employed.

What is claimed is:

1. A disposable test system for testing for the presence of bacterial organisms in a specimen, the system consisting essentially of:
    a buffered substrate solution, for bacterial dehydrogenases in the specimen; and
    an indicator solution for detecting the presence of the bacterial dehydrogenases in the specimen, including
    (a) a tetrazolium salt; and
    (b) phenazine ethosulfate,
    wherein
    (i) the indicator solution is buffered to a pH of approximately 3.3, thereby enhancing the shelf life of the indicator solution,
    (ii) the substrate solution and the indicator solution are not mixed until shortly before use, wherein the shelf-life of the test system is enhanced, and
    (iii) the substrate solution is buffered to a sufficiently high pH so that the test system when mixed has a pH between 8.8 and 9.2, whereby enhanced test sensitivity is achieved without a resulting loss of test specificity.

2. A test system according to claim 1, wherein the substrate solution comprises glucose and at least one amino acid.

3. A test system according to claim 1, wherein the substrate solution consists essentially of glucose, serine, glutamic acid Tris base, anhydrous sodium carbonate and deionized water.

* * * * *